(12) United States Patent
Zhang

(10) Patent No.: US 7,829,132 B2
(45) Date of Patent: Nov. 9, 2010

(54) CONSUMABLE TEA COMPOSITION WITH ANTIOXIDANTS

(75) Inventor: Shi-Qiu Zhang, Tenafly, NJ (US)

(73) Assignee: Unilever Bestfoods, North America division of Conopco, Inc., Englewood Cliffs, NJ (US)

( * ) Notice: Subject to any disclaimer, the term of this patent is extended or adjusted under 35 U.S.C. 154(b) by 358 days.

(21) Appl. No.: 10/980,396

(22) Filed: Nov. 3, 2004

(65) Prior Publication Data

US 2006/0093725 A1 May 4, 2006

(51) Int. Cl.
A23F 3/00 (2006.01)

(52) U.S. Cl. .................. 426/597; 426/590; 426/541

(58) Field of Classification Search ............... 426/597, 426/590, 541
See application file for complete search history.

(56) References Cited

U.S. PATENT DOCUMENTS

| 5,766,595 A * | 6/1998 | Yamane et al. ............. 424/729 |
| 6,254,902 B1 * | 7/2001 | Hodges et al. ............. 426/49 |
| 6,413,570 B1 | 7/2002 | Lehmberg et al. |

| 2002/0001651 A1 | 1/2002 | Norris et al. |
| 2003/0054089 A1 | 3/2003 | Prosise et al. |
| 2004/0097432 A1 * | 5/2004 | Roh-Schmidt et al. ........ 514/27 |
| 2006/0292247 A1 * | 12/2006 | Nishimura et al. .......... 424/729 |

FOREIGN PATENT DOCUMENTS

| EP | 654 221 | 5/1995 |
| EP | 1 297 757 | 4/2003 |
| JP | 2001-302529 | * 10/2001 |
| WO | WO 01/93886 | * 12/2001 |

OTHER PUBLICATIONS

Owuor et al. The changes in black tea quality due to variations of plucking standard and fermentation time. Food Chemistry. vol. 61, No. 4. pp. 435-441.*
Database Abstract—Chemical Abstracts. from Analysis of chemistry during the leaf processing of Baiyaqilan tea. Author: Guo et al. Journal: Jiangzi Nongye Daxue Xuebao. 2003. 25 (1).*
Co-pending application for Zhang et al.; U.S. Appl. No. 10/726,718, filed Dec. 3, 2003.

* cited by examiner

*Primary Examiner*—Anthony Weier
(74) *Attorney, Agent, or Firm*—Edward A. Squillante, Jr.

(57) ABSTRACT

A consumable composition with antioxidants is described. The consumable composition comprises theaflavin, thearubigin and catechin and has good taste and appearance characteristics. The consumable composition can be black tea having green tea catechins as additives.

15 Claims, No Drawings

CONSUMABLE TEA COMPOSITION WITH ANTIOXIDANTS

FIELD OF THE INVENTION

The present invention is directed to a consumable composition. More particularly, the present invention is directed to a consumable composition comprising a mixture of theaflavin, thearubigin and catechin wherein at least about 50.0% by weight of the mixture is theaflavin and thearubigin. The consumable composition of this invention, unexpectedly, has good taste and appearance characteristics, in addition to the many health advantages associated with antioxidants.

BACKGROUND OF THE INVENTION

Excluding water, tea is the most popular beverage consumed by man. Tea is very refreshing, can be served either hot or cold, and has been made commercially available for many years. Lipton®, for example, is the world's leading brand of tea, made available in over 110 countries by Unilever.

Today, modern scientists are exploring the exciting potential of tea, which has a unique combination of natural antioxidants known as flavonoids that can include catechins, flavonols and flavonol glucosides. Taken regularly, tea can help improve vascular function, combat fatigue, reduce cholesterol levels and increase feelings of vitality.

Antioxidants found in tea, especially green tea, are believed to reduce the risk of cancer. In fact, studies indicate that antioxidants lower the risks of cancer in the upper digestive tract, colon, rectum, pancreas and breasts.

Since antioxidants are associated with good health, it is of increasing interest to incorporate antioxidants into consumable compositions. The difficulty, however, is to add antioxidants to consumable compositions without compromising the taste and stability of the same. Particularly, it is of increasing interests to incorporate green tea antioxidants into consumable compositions, and especially, in areas where green tea is not popular. This invention, therefore, is directed to a consumable composition comprising increased levels of antioxidants. The consumable composition of this invention comprises a mixture of theaflavin, thearubigin, and catechin wherein at least about 50.0% by weight of the mixture is theaflavin and thearubigin. The consumable composition of this invention, unexpectedly, has good taste and appearance characteristics, as well as the health advantages associated with antioxidants.

ADDITIONAL INFORMATION

Efforts have been made for making tasty consumable compositions. In U.S. Application Publication No. 2003/0054089 A1, ready-to-eat and tasty foods are described.

Other efforts have been disclosed for making good tasting edible consumables. In U.S. Application Publication No. 2002/0001651 A1, edible consumables with monomeric or oligomeric polyphenolic compounds are described.

Even other efforts have been made for making good tasting consumable compositions. In U.S. application Ser. No. 10/726,718, beverage compositions with improved flavor are described.

Still other efforts have been disclosed for making good tasting consumable compositions. In U.S. Pat. No. 6,413,570, concentrates for good tasting ready-to-drink tea compositions are described.

None of the additional information above describes a consumable composition comprising a mixture of theaflavin, thearubigin and catechin wherein at least about 50.0% by weight of the mixture is theaflavin and thearubigin.

SUMMARY OF THE INVENTION

In a first aspect, the present invention is directed to a consumable composition precursor comprising a polyphenol mixture comprising theaflavin, thearubigin and catechin wherein the polyphenol mixture comprises at least about 50.0% by weight theaflavin and thearubigin.

In a second aspect, the present invention is directed to a consumable composition made from the consumable composition precursor of the first aspect of this invention.

In a third aspect, the present invention is directed to a method for making the consumable composition of the second aspect of this invention.

Consumable composition precursor means a precursor composition used to make a consumable composition. The preferred consumable composition precursor of this invention is black tea concentrate used to make a ready-to-drink tea beverage (i.e., consumable composition).

Consumable composition, as used herein, means a food product ready-to-consume, like a tasty beverage, spread, sauce, dip, spoonable dressing, pourable dressing, ice cream, pasta composition, wheat-based composition (e.g., bread), meal supplement or replacement drink, or a meal supplement or replacement bar. In a preferred embodiment, the consumable composition of this invention is a ready-to-drink black tea beverage.

DETAILED DESCRIPTION OF THE PREFERRED EMBODIMENTS

There is no limitation with respect to the type of polyphenol mixture used in this invention other than that the polyphenol mixture is suitable for use in consumable compositions and one which comprises theaflavin, thearubigin and catechin wherein the polyphenol mixture comprises at least about 50.0% by weight theaflavin and thearubigin based on total weight of the polyphenol mixture. In a preferred embodiment, the polyphenol mixture comprises at least about 5.0% to about 30.0%, and most preferably, from about 8.0% to about 25.0% by weight catechin based on total weight of the polyphenol mixture and including all ranges subsumed therein. In yet another preferred embodiment, at least about 60.0%, and preferably, at least about 75.0% by weight of the total polyphenol mixture is theaflavin and thearubigin.

The type of catechin employed in this invention is limited only to the extent that the catechin is suitable for human consumption. Illustrative examples of the type of catechin suitable for use in this invention are epicatechin, epicatechin gallate, epigallocatechin, epigallocatechin gallate, catechin, and gallocatechin or a mixture thereof. Preferably, the catechins are isolated from green tea or tea leaves, and therefore, are most preferably added as a compound or mixture of compounds and not within a green tea composition. Such catechins may be isolated from green tea or tea leaves via conventional methods which include extraction with water or organic solvents such as food-grade alcohol or ethyl acetate. Also, the catechins can be synthetically made, some are commercially available, and others can be derived from plants (in addition to tea plants) that are members of the catechu gambir (Uncaria family).

The types of theaflavin and thearubigin employed in this invention are limited only to the extent that these polyphenols are suitable for human consumption. Illustrative examples of the types of theaflavins that can be used in this invention include theaflavin, theaflavin-3-gallate, theaflavin-3-0-gallate, and theaflavin-3-3 di-0-gallate or mixtures thereof. Such theaflavins are typically made via the polyphenol oxidase (PPO) dependent oxidative polymerization of tea leaf polyphenols or flavonoids during fermentation of tea leaf to black tea.

Thearubigin used in this invention is suitable for human consumption, and the same is defined to embrace a gallimaufry of indeterminate structures from the monomeric to the polymeric derived by enzymatic oxidation of the flavan-3-ols in fresh tea leaf. The thearubigin used in this invention is preferably water soluble, acidic, and may be rust brown in color. Illustrative examples of the types of thearubigins that may be used in this invention include those derived from theasinensin and/or proanthocyanidin as well as those found in theafulvin fractions.

Thearubigin, like theaflavin, is made via the oxidative polymerization of green tea polyphenols or flavonoids during fermentation of tea leaf to black tea. The theaflavin and thearubigin suitable for use in the consumable compositions of this invention are preferably isolated from black tea. In a preferred embodiment, however, the theaflavin and thearubigin are in black tea (i.e., as the consumable composition) and the preferred catechin or mixtures of catechins is/are combined with the same.

It is particularly noted that in an especially preferred embodiment, there is at least about two (2) times, and preferably, from about 3 to about 4 times more thearubigin than theaflavin in the polyphenol mixture employed in this invention.

A more detailed description of the types of polyphenols suitable for use in this invention may be found in Analysis of Theaflavins and Thearubigins from Black Tea Extract, by Marie-Claude Menet et al., J. Agric. Food Chem. 2004, 52, 2455-2461; Isolation and Analysis of a Polymeric Thearubigin Fraction from Tea, by Richard G. Bailey et al., J. Sci. Food Agric. 1992, 59, 365-375; Thoughts on Thearubigins, by Edwin Haslam, Phytochemistry, 61 (2003), 61-73, the disclosures of which are incorporated herein by reference.

When adding the mixture of polyphenols to a consumable composition, it is preferred that the theaflavin and thearubigin are isolated from black tea and combined with catechin recovered from green tea. The resulting polyphenol mixture may be added to consumable composition precursors like dry spice mixes for sauces and dressings as well as powdered beverage precursors and flours and grains for pastas and breads. Such a polyphenol mixture may also be added to consumable compositions ready for consumption like dips, spoonable dressings and spreads and mixed within the same to yield an antioxidant comprising and homogeneous consumable composition. Typically, the polyphenol mixture comprising theaflavin, thearubigin and catechin makes up from about 0.10% to about 1.0%, and preferably, from about 0.15% to about 0.60%, and most preferably, from about 0.20% to about 0.40% by weight of the total weight of the consumable composition, including all ranges subsumed therein.

In a preferred embodiment, the consumable composition precursor (to which the polyphenol mixture described herein is added or prepared) is a black tea concentrate or extract made commercially available by Unilever under the Lipton Tea brand. The precursor often has from about 5.0 to about 30.0% by weight tea solids and is combined with selected carbohydrates (e.g., high fructose corn syrup and/or corn syrup) in a ratio of 1.5 parts or more of carbohydrate to 1 part of tea solids. Such a precursor (i.e., one used to make a ready to drink tea beverage) is preferably thermally and/or aseptically packaged and typically has a pH from about 3.5 to about 6.0, and preferably, from about 4.0 to about 6.0, including all ranges subsumed therein.

The preferred consumable composition precursor which may be used in this invention is typically prepared by first making a mixture of enzymes suitable to digest the cell walls of tea leaf. Tea leaf is added to the enzyme mixture with water and sent through an extractor to allow for enzyme solution and tea leaf contact time. The resulting leaf slurry is heated to a temperature from about 25° C. to about 98° C., yielding an aqueous tea leaf solution. The same is pasteurized and subjected to centrifugation and concentration in order to recover the desired concentrate. To the concentrate is added (and thoroughly mixed) the catechins described herein and isolated from, for example, green tea.

When the consumable composition precursor of this invention is a tea concentrate, it has been discovered that the same is unexpectedly more stable than tea concentrates not having the polyphenol mixture of this invention. More stable, as defined herein, means suitable to make a ready-to-drink tea beverage with good taste and limited visible haze (Hunter Haze Value under 70) after being stored for about 57 days at about 35° C. as measured on a Hunter DP9000 Spectrophotometer in a 5 cm cell.

The resulting tea concentrate may then be diluted with water to produce a consumable black tea composition with good taste and appearance characteristics. Such a consumable black tea composition is translucent, healthy and free of precipitate like white alcoholic precipitate. A more detailed description of the preparation of the consumable composition precursors (not having the mixture of polyphenols described herein) is found in U.S. Pat. No. 6,413,570, the disclosure of which is incorporated herein by reference.

It is within the scope of this invention to employ optional additives like a chelator, colorant, preservative, flavor, vitamin, sweetener, fruit juices, surfactant (like sorbitan monolaurate and sorbitan monopalmitate), acidulant and the like. When employed, such optional additives, collectively, make up less than about 15.0% by weight of the total weight of the consumable composition precursor.

A type of dispenser suitable for use with the superior tea concentrate of this invention is one which combines concentrate with a liquid, like water, in order to produce a ready to drink tea beverage. Such a dispenser typically combines about one (1) part of tea concentrate to about 95 to about 100 parts by weight liquid in order to produce the desired consumable composition. A more detailed description of the type of dispenser suitable for use in this invention is described, for example, in U.S. Pat. Nos. 6,792,847, and 6,685,059, and U.S. Patent Application No. 2003/0116025, the disclosures of which are incorporated herein by reference.

The following examples are provided to facilitate an understanding of the present invention. The examples are not intended to limit the scope of the claims.

EXAMPLE 1

A consumable composition precursor (tea concentrate) having the following ingredients was made:

| Ingredient | Percent by Weight (%) |
| --- | --- |
| Black tea solids | 32.40 |
| Preservative | 0.20 |
| Color | 0.64 |

-continued

| Ingredient | Percent by Weight (%) |
|---|---|
| Acidulant | 0.55 |
| Corn syrup (72%) | 40.71 |
| Catechin* | 0.70 |
| Water | Balance |

*Isolated from green tea and mixed in the precursor.

The consumable composition precursor was packaged in a commercially available package and dispensed from an apparatus similar to the one described in U.S. Patent Application No. 2003/0116025. The resulting ready-to-drink black tea consumable composition was made by combining and dispensing one part precursor for every 100 parts of water.

EXAMPLE 2

Ready-to-drink black tea consumable compositions similar to the ones described in Example 1 were made from precursors stored at 35° C. for 57 days along with control precursors kept at the same conditions and having no added catechins. The resulting ready-to-drink black tea consumable compositions made from the consumable composition precursor of this invention unexpectedly had Hunter Haze Values under 70, whereas the resulting ready-to-drink black tea consumable compositions made with control precursors all had Hunter Haze Values over 80 (commercially unacceptable). The results indicate that the polyphenol mixture described herein unexpectedly results in a stable precursor which leads to a consumable composition having an appearance more acceptable to consumers.

EXAMPLE 3

Ready-to-drink black tea consumable compositions were made with precursors similar to the one described in Example 1. Control ready-to-drink black tea consumable compositions were made with precursors like the one described in Example 1 except that no catechin was added. The precursor having catechin added thereto was aged to about six months prior to making the ready-to-drink black tea consumable compositions of this invention. The controls were made with precursor that was no more than one month old.

Both ready-to-drink black tea consumable compositions were sampled by trained panelists for Quantitative Descriptive Analysis. The panelists unanimously concluded that the ready-to-drink black tea consumable compositions made according to this invention (and with about six month old precursor) had the same residue astrigency, residue bitterness and other flavor attributes as did control ready-to-drink consumable compositions made from precursor that was not more than one month old.

The results indicate that the consumable composition precursors made according to this invention are unexpectedly stable, leading to a consumable composition with increased levels of antioxidants and with characteristics similar to conventional consumable compositions made with a conventional precursor that is five times fresher or newer.

What is claimed is:

1. A black tea precursor, the precursor comprising:
   (a) a polyphenol mixture comprising theaflavin and thearubigin in black tea, and added catechin recovered from green tea or tea leaf, wherein the polyphenol mixture comprises at least about 60.0% theaflavin and thearubigin by weight of the polyphenol mixture, and
   (b) at least 1.5 parts of carbohydrate to one part of tea solids,
   wherein the precursor is stable and is a concentrate or extract comprising from about 5.0 to about 30.0% by weight tea solids.

2. The black tea precursor according to claim 1 wherein there is at least about two times more thearubigin than theaflavin.

3. The black tea precursor according to claim 1 wherein the polyphenol mixture comprises from about 5.0% to about 30.0% by weight catechin, based on total weight of the polyphenol mixture.

4. A consumable black tea composition comprising the precursor of claim 1 and water.

5. The consumable composition according to claim 4 wherein the polyphenol mixture comprises from about 5.0% to about 30.0% by weight catechin.

6. The consumable composition according to claim 4 wherein there is at least about two times more thearubigin than theaflavin in the polyphenol mixture.

7. The consumable composition according to claim 4 wherein the polyphenol mixture makes up from about 0.10% to about 10% by weight of the total weight of the consumable composition.

8. The consumable composition according to claim 4 wherein the consumable composition is a ready-to-drink black tea.

9. The consumable composition according to claim 4 wherein the catechin is a green tea polyphenol.

10. The consumable composition according to claim 4 wherein the consumable composition has a Hunter Haze Value of under 70 after being stored for about 57 days at about 35° C.

11. The consumable composition according to claim 4 wherein the consumable composition has no precipitate.

12. The black tea precursor according to claim 1 wherein carbohydrate is high fructose corn syrup, corn syrup or a mixture thereof.

13. The consumable composition according to claim 4 wherein carbohydrate is high fructose corn syrup, corn syrup or a mixture thereof.

14. The composition black tea composition precursor according to claim 1 wherein the polyphenol mixture comprises at least about 75% by weight theaflavin and thearubigin.

15. The consumable black tea composition according to claim 4 wherein the polyphenol mixture comprises at least about 75% by weight theaflavin and thearubigin.

* * * * *